United States Patent
Castro Miller et al.

(10) Patent No.: US 10,398,333 B2
(45) Date of Patent: Sep. 3, 2019

(54) DEVICE AND METHOD FOR CONTROLLING ACQUISITION OF A SIGNAL AND A SYSTEM FOR ACQUISITION OF A SIGNAL

(71) Applicants: IMEC VZW, Leuven (BE); Katholieke Universiteit Leuven, KU LEUVEN R&D, Leuven (BE)

(72) Inventors: Ivan Dario Castro Miller, Gentbrugge (BE); Tom Torfs, Kraainem (BE)

(73) Assignees: IMEC VZW, Leuven (BE); Katholieke Universiteit Leuven, KU LEUVEN R&D, Leuven (BE)

( * ) Notice: Subject to any disclaimer, the term of this patent is extended or adjusted under 35 U.S.C. 154(b) by 93 days.

(21) Appl. No.: 15/589,496

(22) Filed: May 8, 2017

(65) Prior Publication Data
US 2017/0325701 A1    Nov. 16, 2017

(30) Foreign Application Priority Data
May 12, 2016    (EP) .................................... 16169419

(51) Int. Cl.
*A61B 5/00*    (2006.01)
*A61B 5/04*    (2006.01)
(Continued)

(52) U.S. Cl.
CPC ........ *A61B 5/04012* (2013.01); *A61B 5/0452* (2013.01); *A61B 5/18* (2013.01);
(Continued)

(58) Field of Classification Search
CPC ........ A61B 2562/0214; A61B 5/04012; A61B 5/0452; A61B 5/18; A61B 5/6892;
(Continued)

(56) References Cited

U.S. PATENT DOCUMENTS

2007/0100278 A1*    5/2007    Frei .................... A61B 5/04012
                                                                    604/66

FOREIGN PATENT DOCUMENTS

EP    2 591 720 A1    5/2013

OTHER PUBLICATIONS

Li, Qiao et al., "Robust Heart Rate Estimation from Multiple Asynchronous Noisy Sources Using Signal Quality Indices and a Kalman Filter", Physiol Meas., vol. 29(1), Jan. 2008, pp. 15-32.
(Continued)

*Primary Examiner* — George Manuel
(74) *Attorney, Agent, or Firm* — McDonnell Boehnen Hulbert & Berghoff LLP

(57) ABSTRACT

Devices, systems, and methods for controlling acquisition of a signal representing a physiological measurement are described herein. An example device comprises: an input for receiving the signal in digital form, wherein the signal has been acquired by means of at least one electrode without galvanic contact between the electrode and the living being and has been processed by circuitry for acquisition of the signal in analog domain to refine the signal before the signal is converted from analog to digital domain; an adaptation decision module, being configured to determine whether a measure of signal quality indicates that an adaptation of the circuitry for acquisition of the signal in analog domain is beneficial for the robustness of the system and/or the quality of the obtained signals; wherein the adaptation decision module, is arranged to output a control signal for controlling a parameter affecting amplifier saturation in processing of the signal.

19 Claims, 8 Drawing Sheets

(51) Int. Cl.
*A61B 5/0452* (2006.01)
*A61B 5/18* (2006.01)

(52) U.S. Cl.
CPC .......... *A61B 5/6893* (2013.01); *A61B 5/7221* (2013.01); *A61B 5/7225* (2013.01); *A61B 5/6892* (2013.01); *A61B 2562/0214* (2013.01)

(58) Field of Classification Search
CPC ... A61B 5/6893; A61B 5/7221; A61B 5/7225; A61B 5/0245; A61B 5/0428; A61B 5/04286; A61B 5/0432; A61B 5/04525; A61B 5/6844; A61B 5/7203; A61B 5/7217; A61B 5/7267; A61B 5/7285; A61N 5/1068
See application file for complete search history.

(56) References Cited

OTHER PUBLICATIONS

Zimetbaum, Peter J. et al., "Diagnostic Yield and Optimal Duration of Continuous-Loop Event Monitoring for the Diagnosis of Palpitations, A Cost-Effectiveness Analysis", Ann. Intern. Med., vol. 128, No. 11, Jun. 1, 1998, pp. 890-895.

* cited by examiner

DEVICE AND METHOD FOR CONTROLLING ACQUISITION OF A SIGNAL AND A SYSTEM FOR ACQUISITION OF A SIGNAL

CROSS-REFERENCE TO RELATED APPLICATIONS

The present application is a non-provisional patent application claiming priority to EP Patent Application No. 16169419.5, filed May 12, 2016, the contents of which are hereby incorporated by reference.

FIELD OF THE DISCLOSURE

The present disclosure relates to a device and method for controlling acquisition of a signal representing a physiological measurement of a living being, and a system for acquisition of a signal. In particular, the disclosure relates to controlling acquisition of a signal by means of at least one electrode without galvanic contact between the electrode and the living being.

BACKGROUND

Acquisition of signals representing a physiological measurement of a living being is important or of interest in many contexts. The signals may be used in clinical settings to provide information for treatment of the living being, but may also be used for general monitoring of a physical condition of the living being. For instance, biopotential acquisition (electrocardiography, electroencephalography, electromyography, etc) and other biological-related measurements (photoplethysmography, bioimpedance, etc) are of interest.

Sensors for contactless measurements may be used for providing higher comfort to a person wearing the sensors, for performing long term recordings, and/or for a reduced set-up time of the sensor.

One problem in acquisition of signals representing a physiological measurement is presence of motion artifacts. In ambulatory measurements, such a problem may be accentuated.

Further, when using contactless measurements, motion artifacts may be especially severe. In contactless measurements, the acquired signal may need to be amplified to a relatively high degree. Also, there may be a relative movement between a contactless sensor and the living being, which may contribute to the motion artifacts. Motion artifacts may thus cause saturation of amplifiers within circuitry used for acquisition and preprocessing of the signal, which prevents any analysis of the signal.

Thus, it would be desired to have a system for acquisition of signals representing physiological measurements, which is more robust to motion artifacts.

In EP 2591720, a biomedical acquisition system with motion artifact reduction is disclosed. The system comprises a digital adaptive filter unit configured to calculate a digital motion artifact estimate, at least one digital-to-analog converter configured to convert the digital motion artifact estimate to an analog signal, and a feedback loop for sending the analog motion artifact estimate signal to a readout channel configured to deduct the analog motion artifact estimate signal from an analog measured ECG signal. However, if noise estimation in this system is not accurate, there is actually a risk of saturating an amplifier by means of the feedback signal.

SUMMARY

It is an object of the present disclosure to provide a control of acquisition of signals representing physiological measurements, which is robust. It is further object to provide a control which is dynamically adaptable, in particular in view of environmental conditions.

These and other objects of the present disclosure are set forth, at least in part, as defined in the independent claims. Aspects of additional or alternative embodiments are set out in the dependent claims.

According to a first aspect of the present disclosure, there is provided a device for controlling acquisition of a signal representing a physiological measurement on a living being; the device comprising: an input for receiving the signal in digital form, wherein the signal has been acquired by means of at least one electrode without galvanic contact between the electrode and the living being and has been processed by circuitry for acquisition of the signal in analog domain to refine the signal before the signal is converted from analog to digital domain; a signal quality calculation module, being configured to calculate at least one measure of signal quality based on the received signal; an adaptation decision module, being configured to determine whether the at least one measure of signal quality indicates that an adaptation of the circuitry for acquisition of the signal in analog domain is beneficial; wherein the adaptation decision module, in response to the determination that an adaptation of the circuitry for acquisition of the signal is beneficial, is arranged to output a control signal for controlling a parameter of the circuitry for acquisition of the signal in analog domain, wherein the controlled parameter is a parameter affecting amplifier saturation in processing of the signal by the circuitry.

According to a second aspect of the present disclosure, there is provided a computer program product comprising a computer-readable medium with computer-readable instructions such that when executed on a processing unit the computer program product will cause the processing unit to perform a method for controlling acquisition of a signal representing a physiological measurement on a living being, the method comprising: receiving the signal in digital form, wherein the signal has been acquired by means of at least one electrode without galvanic contact between the electrode and the living being and has been processed by circuitry for acquisition of the signal in analog domain to refine the signal before the signal is converted from analog to digital domain; calculate at least one measure of signal quality based on the received signal; determine whether the at least one measure of signal quality indicates that an adaptation of the circuitry for acquisition of the signal in analog domain is beneficial; in response to the determination that an adaptation of the circuitry for acquisition of the signal is beneficial, output a control signal for controlling a parameter of the circuitry for acquisition of the signal in analog domain, wherein the controlled parameter is a parameter affecting amplifier saturation in processing of the signal by the circuitry.

In some embodiments, it is determined whether an adaptation of circuitry for acquisition of a signal representing a physiological measurement in analog domain is beneficial and a control signal for controlling a parameter of the circuitry is output. Hence, hardware for acquiring the signal in analog domain may be dynamically adapted in real-time based on the signal quality. The control of the parameter may thus attempt to prevent amplifier saturation.

For instance, a gain of an amplifier or a filter cut-off frequency may be controlled to prevent saturation of the signal. This implies that a trade-off in signal quality is made when there is a risk of saturation of the acquired signal. However, thanks to a dynamic adaptation of the circuitry, a lower quality signal need only be acquired when necessary or in some way beneficial to the signal processing.

Thus, according to the present disclosure, acquisition of signals representing physiological measurements may be made robust, e.g. to motion artifacts, as the acquisition may be controlled to obtain a signal of a quality that is adapted to prevailing conditions.

Although the controlled parameter is a parameter affecting amplifier saturation, the adaptation of the circuitry could also target an improvement on signal quality and/or ease of feature extraction from the acquired signal. Thus, the adaptation of the circuitry may ensure that acquisition of signals is robust against motion artifacts and that the signal quality is fit for further analysis.

Some embodiments described in the present disclosure may be particularly useful for acquiring physiological measurements on a person, e.g. a patient in a clinical or ambulatory setting, or a person on which a physiological parameter is monitored. However, it should be realized that other embodiments described herein may also be used on animals, e.g. for monitoring cattle for stress or diseases.

Thanks to the robustness of the device, e.g. to motion artifacts, the device provides an increased freedom in arranging a sensor for acquiring physiological measurements in relation to the living being and in relation to a noisy environment. Thus, the device could allow a sensor to be mounted to provide long-term monitoring of a person without affecting daily life of the person, such as mounting the sensor in a seat of a car, in an office chair, in a mattress, or in a garment worn by the person. Thus, the person may be monitored without even noticing that a sensor is mounted in relation to the person and the device may ensure that a useful signal may be acquired even though motion artifacts may be common.

Some embodiments may include controlling acquisition of a signal which is acquired by means of at least one electrode without galvanic contact and which is processed by circuitry in analog domain to refine the signal. Thus, embodiments of the present disclosure may be arranged for controlling contactless measurements, such as electrodes being not in direct contact with the living being and, for instance, acquiring a signal by capacitive coupling to the living being. However, it should be realized that the electrode may be in contact with the living being, e.g. by being integrated in clothes, while still not in galvanic contact with the living being.

Further, the circuitry for acquisition of the signal in analog domain may comprise a plurality of components for refining the signal before it is converted to digital domain. The control signal may control a parameter of the circuitry such that amplifier saturation in processing of the signal is affected. Thus, one or more of the components of the circuitry may be affected by the control signal such that amplifier saturation may be avoided or prevented.

According to an embodiment, the controlled parameter is at least one in the group of: a gain of an amplifier, a cut-off frequency of a filter, and a gain of an active feedback circuitry. These parameters may affect amplifier saturation.

The gain of the amplifier may directly affect a risk of saturation. For instance, by decreasing the gain, the smaller signal amplitude may prevent saturation, but the signal-to-noise ratio may be decreased. Thus, the amplifier signal may not be saturated, which allows the signal to be analyzed, but the signal-to-noise ratio may be poorer in comparison to using a higher gain.

The cut-off frequency of a filter may determine which frequencies are allowed to pass to an amplifier. Thus, the control parameter may control the filter to cut-off low frequencies, which may prevent motion artifacts in low frequencies to be passed to the amplifier. Thereby, such motion artifacts may be removed. On the other hand, signal information in the cut-off frequencies is lost.

The gain of an active feedback circuitry may control an impact of the active feedback circuitry in two cases. In the first case, by reducing the gain of the active feedback circuitry, it may be ensured that oscillations, or other noise present in the feedback does not cause a too strong signal to be acquired and, hence, amplifier saturation may be avoided or prevented. In the second case, by increasing the gain of the active feedback circuitry, it may be ensured that common-mode artifacts are compensated for, and, hence amplifier saturation may be avoided or prevented. The analysis of this trade-off is performed by the adaptation decision module.

The adaptation decision module may determine whether a measure of signal quality indicates that an adaptation of the circuitry is beneficial for the robustness of the system and/or the quality of the obtained signals. The adaptation of the circuitry may be beneficial in terms of robustness of the acquiring of the signal and the control signal may thus control a parameter of the circuitry for ensuring that an amplifier saturation does not occur. However, the measure of the signal quality may also indicate that a risk of amplifier saturation has decreased, such that adaptation of the circuitry may be beneficial in terms of controlling the circuitry such that more detailed information is obtained.

According to an embodiment, the device further comprises a feature extraction analysis module, being configured to receive input from the adaptation decision module on the signal quality of the received signal and to determine features that are extractable from the received signal.

This implies that the device may be able to extract features in correspondence to a quality of the received signal. Thus, if the acquisition of the signal is controlled in order to prevent amplifier saturation such that the signal information obtained is reduced, the feature extraction analysis module may simultaneously determine which features may still be successfully extracted from the signal. Hereby, the signal may be analyzed in a manner corresponding to the information that is contained in the signal. For instance, in acquisition of an ECG signal, the feature extraction analysis module may determine whether a full ECG waveform morphology may be analyzed or whether only R-peak detection and/or heart rate and heart rate variability determination is possible. In another example, in acquisition of a bioimpedance signal for respiratory monitoring, the feature extraction analysis may determine whether waveform-dependent characteristics, such as respiration volume, may be determined or whether only respiration rate or respiration rate variability determination is possible.

According to an embodiment, the adaptation decision module is configured to receive input from auxiliary sensors and is further configured to consider the received input from auxiliary sensors in determining whether an adaptation of the circuitry for acquisition of the signal in analog domain is beneficial. The auxiliary sensors may provide information of movement of the living being, of the sensing electrodes, or an environment in which the living being is. Thus, the auxiliary sensor may contribute to determine when amplifier saturation is likely, and the adaptation decision module may use the input from auxiliary sensors to prevent amplifier saturation by controlling the circuitry before amplifier saturation occurs.

According to an embodiment, the adaptation decision module is configured to compare the at least one measure of signal quality to a threshold value and determine whether the at least one measure of signal quality indicates that an adaptation of the circuitry for acquisition of the signal is beneficial based on a relation between the at least one measure and the threshold value. The threshold value may thus provide a reference value indicating when adaptation of the circuitry may be beneficial.

According to an embodiment, a plurality of measures of signal quality are obtained. The plurality of measures may be compared to respective threshold values and a combination of results of such comparisons may be used for deciding whether adaptation of the circuitry is beneficial.

According to an embodiment, the acquired signal is a measurement of capacitively coupled electrocardiogram (ccECG). A ccECG may be useful for ambulatory use, e.g. for continuous monitoring of electrical activity of the cardiovascular system similar to a Holter monitor. For instance, the ccECG may be used for home monitoring of a person. Electrodes may then be embedded in mobiliary, such as in an office chair, a car, a mattress/bed sheets, etc. A system for contactless measurements may be particularly useful for long-term measurements (where gel of an electrode directly applied to the body can dry out and is not comfortable, and cables attached are cumbersome to wear).

By means of a dynamically adapted acquisition of the ccECG signal, acquiring of the signal may be enabled while varying the robustness and signal quality according to what is more beneficial for the robustness of the system and/or the quality of the obtained signals. Thus, a ccECG signal containing a full standard-compliant ECG waveform morphology may be obtained when possible, without the signal being saturated when affected by large motion artifacts such that a useful signal is still obtained in such circumstances.

However, it should be realized that the acquired signal may be another measurement, such as an electroencephalogram (EEG), electromyogram (EMG), or bioimpedance (BIOZ). For instance, a BIOZ measurement may be used for respiratory monitoring, as a magnitude of a BIOZ measurement may represent electrical impedance of a person's thorax, which changes within each respiration cycle, and may be used for extraction of respiratory rate and estimation of respiration (tidal) volume.

According to an embodiment, the acquired signal is a measurement of capacitively coupled BIOZ in relation to a thoracic area of a person. By detecting electrical impedance in the thoracic area of the person, respiratory monitoring may be performed. A ccBIOZ measurement may be useful for ambulatory use, e.g. for continuous monitoring of respiratory rate and/or pattern, e.g. for sleep monitoring.

By means of a dynamically adapted acquisition of the ccBIOZ signal, acquiring of the signal may be enabled while varying the robustness and signal quality according to what is more beneficial for the robustness of the system and/or the quality of the obtained signals. Thus, a ccBIOZ signal containing a full waveform morphology may be obtained when possible, without the signal being saturated when affected by large motion artifacts such that a useful signal (e.g. allowing determination of respiratory rate) is still obtained in such circumstances.

According to a third aspect of the present disclosure, there is provided a system for acquisition of a signal representing a physiological measurement on a living being, the system comprising: a device according to the first aspect; a sensor for obtaining a physiological measurement on a living being, the sensor comprising at least one electrode arranged to acquire a signal representing physiological measurement without the at least one electrode being in galvanic contact between the electrode and the living being; and processing circuitry for processing the signal representing the obtained physiological measurement.

According to a fourth aspect of the present disclosure, there is provided a method for acquisition of a signal representing a physiological measurement on a living being, the method comprising: obtaining a physiological measurement on a living being using a sensor comprising at least one electrode arranged to acquire a signal representing physiological measurement without the at least one electrode being in galvanic contact between the electrode and the living being; processing the signal to refine the signal in analog domain; converting the refined signal to digital form; calculating at least one measure of signal quality based on the signal in digital form; determining whether the at least one measure of signal quality indicates that an adaptation of circuitry for acquisition of the signal in analog domain is beneficial; and outputting a control signal for controlling a parameter for processing of the signal to refine the signal in analog domain.

According to an embodiment of the method, the controlled parameter is a parameter affecting amplifier saturation in processing of the signal.

The system thus incorporates the device for controlling acquisition of a signal representing a physiological measurement on a living being with a sensor for obtaining the physiological measurement. Similarly, the method includes obtaining of the physiological measurement and determining whether the circuitry for acquisition of the signal is to be controlled.

Certain aspects of the system and method of the third and fourth aspects of the present disclosure are largely analogous with aspects described above in connection with the first and second aspect of the present disclosure.

According to an embodiment of the system, the processing circuitry comprises an amplifier for amplifying the signal.

According to another embodiment, the processing circuitry comprises a filter for filtering out undesired frequencies of the signal.

According to yet another embodiment, the processing circuitry further comprises an active feedback circuitry comprising an electrode being arranged for providing an active feedback signal to the living being.

The processing circuitry may be arranged to comprise one or more of the above components. As explained above, the control parameter may be used for controlling one or more of the above components for adapting the circuitry based on a measure of signal quality.

According to an embodiment, the system may further comprise an auxiliary sensor for detecting a movement of the living being or a relative movement of the sensor and the living being. The auxiliary sensor may be connected to the device for contributing to the determination whether an adaptation of the circuitry is beneficial for the robustness of the system and/or the quality of the obtained signals.

According to an embodiment, the system may further comprise a feature extraction module, configured to receive the signal in digital form and receive input from a feature extraction analysis module regarding features that are extractable from the received signal, the feature extraction module being configured to process the received signal based on the input from the feature extraction analysis module.

Thus, the system may, by means of the feature extraction module, be arranged to extract features that are included in the received signal for analysis of the signal. Hence, the system may be completely automatic in that the circuitry is adapted to obtain a signal of a quality that is dependent on the conditions in which the signal is obtained and an analysis of the signal is based on the available features in the acquired signal and the available features may be extracted and presented as output from the system.

According to a fifth aspect of the present disclosure, there is provided a car-installed condition monitoring system for monitoring a person, the condition monitoring system comprising: a device according to the first aspect; a sensor for obtaining a physiological measurement on the person, the sensor comprising at least one electrode arranged to acquire a signal representing physiological measurement without the at least one electrode being in galvanic contact between the electrode and the person, the sensor being mounted in a seating of the car for monitoring the person while seated in the seating; and processing circuitry for processing the signal representing the obtained physiological measurement.

The car-installed condition monitoring system enables acquiring a signal representing a physiological measurement of a person while seated in the car. Thanks to the robustness of the device, a non-saturated signal may be acquired for large percentages of time, even though motion artifacts could be caused e.g. when driving in a non-paved road or a road with holes and bumps.

Further, condition monitoring installed in a car may be used for improving secure driving of the car and/or for providing health information to the driver (or a passenger). Thus, the car-installed condition monitoring system could be used for detecting an electrical heart activity and/or respiratory activity e.g. for performing a daily health checkup of a driver (for instance, during driving the car to work) for monitoring the health of the driver. The health checkup may allow a car owner to periodically check a health condition and to identify illness or a condition at an early stage. The car-installed condition monitoring system could also or alternatively be used for monitoring the driver in determining whether a condition of the driver is unfit for driving the car, e.g. by the system monitoring for drowsiness or attention level of a driver, performing stress detection, using the monitoring as an input in a semi-autonomous car, or detecting sudden health anomaly of the driver. The car-installed condition monitoring system may also be used in post-accident driver assessment, e.g. for determining a cause of an accident.

The car-installed condition monitoring system may be incorporated or integrated in an overall car control system. Thus, the device of the car-installed condition monitoring system may be implemented in a processing unit shared by numerous components of the car control system.

The car-installed condition monitoring system may provide input which may be combined by other input from other sensors so that the car control system may take actions or perform assessments based on plural input. For instance, monitoring for drowsiness or attention level of a driver may be based on plural inputs, e.g. using also a camera imaging a face of the driver.

According to a sixth aspect of the present disclosure, there is provided a sleep monitoring system, comprising: a device according to the first aspect; a sensor for obtaining a physiological measurement on a person, the sensor comprising at least one electrode arranged to acquire a signal representing physiological measurement without the at least one electrode being in galvanic contact between the electrode and the person, the sensor being mounted in a mattress or bed linen for monitoring the person while lying on the mattress; and processing circuitry for processing the signal representing the obtained physiological measurement.

The sleep monitoring system enables acquiring a signal representing a physiological measurement of a person while lying on a mattress, sleeping. Thanks to the robustness of the device, a non-saturated signal may be acquired for large percentages of time, even though motion artifacts could be caused e.g. by changes in position of the person or by heavy respiration.

The sleep monitoring system enables the sensor to be mounted in a mattress, such that the sleep monitoring system need not affect comfort of the person.

Sleep monitoring using physiological measurements e.g. relating to heart activity and respiration, may be useful in aiding a person to sleep better and may also be useful as a tool for monitoring a health condition of the person, potentially identifying sleep-related diseases such as sleep apnea. Monitoring of the health condition can be performed during a long screening time at the person's home under comfortable conditions, and could be an additional tool to polysomnography (PSG) tests, which need to be performed at a hospital and therefore are limited in time and with reduced comfort.

A sensor for obtaining a physiological measurement on a person may in other applications be mounted e.g. in an office chair or in a garment.

Mounting the sensor in an office chair may allow monitoring of a person while working, which may be useful for stress detection and management. The device for controlling acquisition of a signal representing a physiological measurement on the person may be used for adaptation of the acquisition so as to allow acquiring useful signals in view of characteristic motions of the person while seated in the office chair, such as changing positions or typing.

Mounting the sensor in a garment, such as a jacket or shirt, may allow continuous monitoring of a person when wearing the garment. Thus, the person may be monitored and the device for controlling acquisition of a signal representing a physiological measurement on the person may be used for adaptation of the acquisition so as to allow acquiring useful signals in view of different contexts, such as the person walking, sitting, typing, etc.

BRIEF DESCRIPTION OF THE FIGURES

The above, as well as additional, features will be better understood through the following illustrative and non-limiting detailed description of example embodiments, with reference to the appended drawings.

All the figures are schematic, not necessarily to scale, and may show parts that elucidate example embodiments, wherein other parts may be omitted or merely suggested.

DETAILED DESCRIPTION

Example embodiments will now be described more fully hereinafter with reference to the accompanying drawings. That which is encompassed by the claims may, however, be embodied in many different forms and should not be construed as limited to the embodiments set forth herein; rather, these embodiments are provided by way of example. Furthermore, like numbers refer to the same or similar elements or components throughout.

Figure 1:
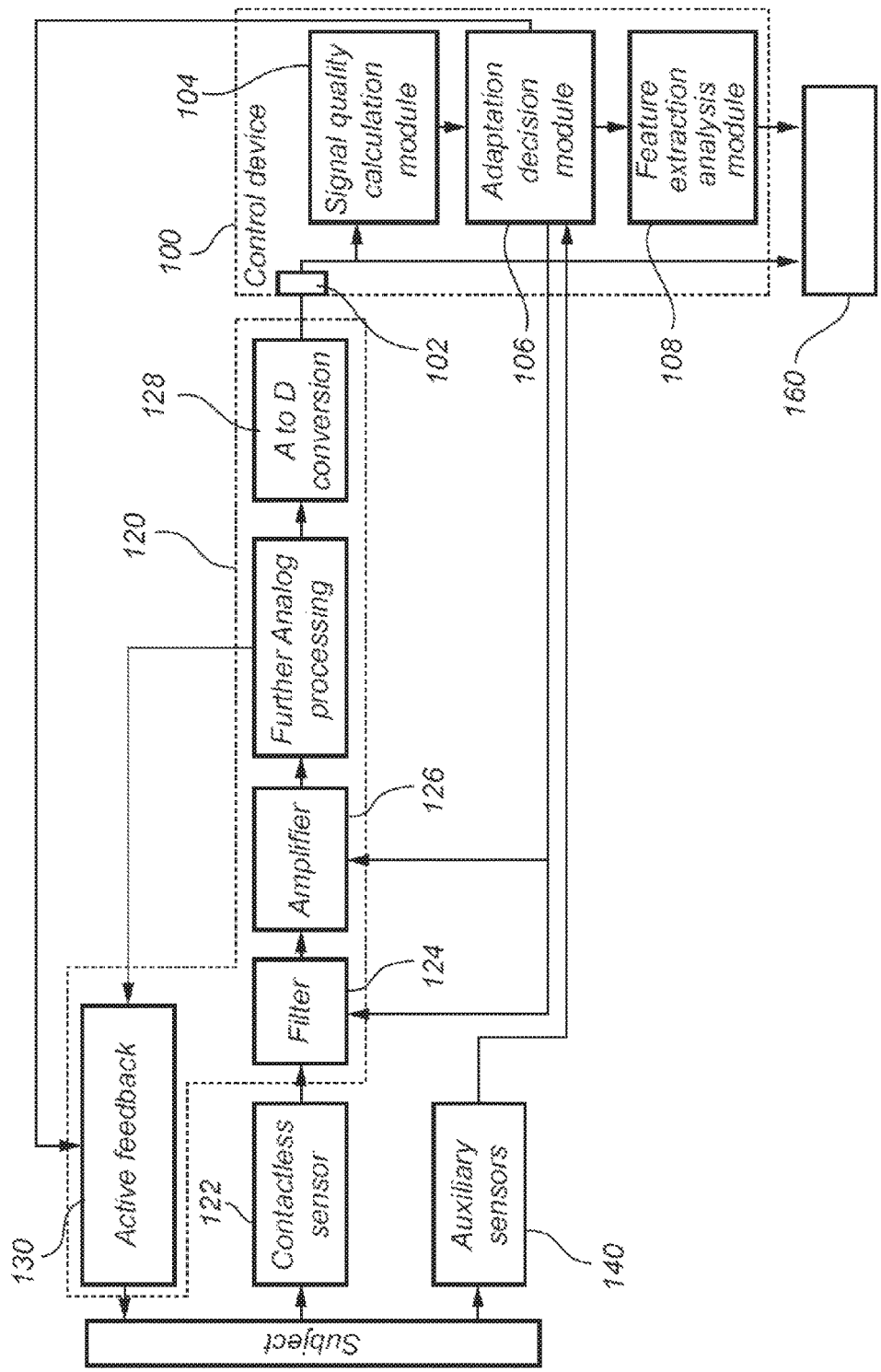
FIG. 1 is a schematic view of a system for acquisition of a signal representing a physiological measurement on a living being including a control device according to an embodiment.

Referring now to FIG. 1, acquisition of a signal representing a physiological measurement on a living being is controlled. The signal may be acquired by at least one electrode without galvanic contact between the electrode and the living being. Thus, the acquired signal may be especially sensitive to motion artifacts. The control of the acquisition of the signal therefore is arranged to provide robustness to the acquisition.

As shown in FIG. 1, a control device 100 may control acquisition of the signal. The control device 100 comprises an input 102 which is arranged to receive the acquired signal in digital form. The control device 100 may thus process the signal in digital form and based on such processing a circuitry 120 for acquisition of the signal in analog domain may be controlled in real-time for dynamically adapting the acquisition.

The control device 100 may be implemented in hardware, or as any combination of software and hardware. The device 100 may, for instance, be implemented as software being executed on a general-purpose computer, as firmware arranged e.g. in an embedded system, or as a specifically designed processing unit, such as an Application-Specific Integrated Circuit (ASIC) or a Field-Programmable Gate Array (FPGA). In a specific embodiment, the device 100 is arranged in a processing unit of a computer, which is connected to the circuitry 120 for acquisition of the signal, the computer being provided with a computer program for controlling the processing unit to perform a process for determining whether an adaptation of the circuitry for acquisition of the signal is beneficial for the robustness of the system and/or the quality of the obtained signals and, if so, to output a control signal for controlling a parameter of the circuitry 120.

The control device 100 may be arranged to receive the signal through a wired or a wireless connection to the circuitry for acquisition of the signal in analog domain.

The control device 100 comprises a signal quality calculation module 104. The signal quality calculation module 104 is arranged to calculate at least one measure of signal quality based on the signal received at the input 102. The at least one calculated measure may be transmitted to an adaptation decision module 106.

The signal quality calculation module 104 may be configured to calculate multiple measures in real-time based on the received signal. These measures may be direct indications, by themselves, of the quality of the signal or may in conjunction provide indications of the quality. The measures may be useful in different conditions, so that, depending on the conditions in which the signal is acquired, different measures may be used for assessing the quality of the signal.

For a signal indicative of heart activity, such as an electrocardiogram, the measures may include, but are not limited to:

spectral density ratio (SDR): ratio of spectrum in selected bands of interest;

Kurtosis and Kurtosis-based signal quality index (kSQI): based on shape of distribution;

beat signal quality index (bSQI): based on a match comparison between two or more different beat detector algorithms with different sensitivity to noise and artifacts;

heart rate (HR) and heart rate variability (HRV) signal quality index (hrSQI, hrvSQI): detection of HR and HRV values that are likely to be out of physiological limits;

correlation signal quality index (corrSQI): based on averaging of QRS segments and back correlating to each of the QRS segments used in averaging in order to determine individual beat quality and averaging qualities over a determined time frame; and autocorrelation of the acquired signal: time periodicity of the heart signal can give an indication of quality.

Similarly, for a signal indicative of respiration, such as a bioimpedance measurement, the measures may include, but are not limited to:

spectral density ratio (SDR): ratio of spectrum in selected bands of interest;

Kurtosis and Kurtosis-based signal quality index (kSQI): based on shape of distribution;

respiration rate based: detection of respiration rate values that are likely to be out of physiological limits; and autocorrelation of the acquired signal: time periodicity of the respiration signal can give an indication of quality.

The signal quality calculation module 104 may be configured to calculate one or more of the quality indicating measures listed above. However, the signal quality calculation module 104 may further be configured to combine, e.g. by optimized fusion, one or more quality indicating measures for generating different unified metrics that combine aspects of the individual quality indicating measures and may lower inaccuracies (in specific conditions) of the individual quality indicating measures.

The signal quality calculation module 104 may combine quality indicating measures using e.g. data fusion techniques, such as Bayesian networks, probabilistic grids or Kalman filters, decision support tools, or mathematical or logical combinations of quality indicating measures considering individual characteristics and potential usefulness of the quality indicating measures.

One specific example of combinations of quality measures is presented below with reference to FIG. 4. However, it should be realized that many other combinations of measures may be used, using one or more of the measures indicated above.

The adaptation decision module 106 may, in addition to the at least one calculated measure of signal quality (individual or combined measure), receive input also from auxiliary sensors 140. The auxiliary sensors 140 may provide information of movement of the living being, of the sensing electrodes, or an environment in which the living being is and may thus contribute to determination whether the circuitry 120 may need to be adapted to prevailing conditions.

The auxiliary sensors 140 may for instance be arranged to obtain signals related to acceleration, angular velocity, optical absorption/reflection, and capacitance/impedance of a sensor-body interface. The auxiliary sensors 140 may include, but is not limited to, detection of 3-axis acceleration from each electrode, 3-axis angular velocity from each electrode; capacitive electrode-tissue impedance from each electrode pair; force (pressure) from each electrode and proximity measures between the electrode and the living being, e.g. optical-based proximity readings.

The adaptation decision module 106 may use an algorithm for analyzing received input in order to determine whether a parameter of the circuitry 120 is to be controlled. The algorithm may thus provide rules for determining, based on the received input, whether a parameter is to be controlled. For instance, the algorithm may include comparison between the measure of signal quality and a threshold value for determining whether the at least one measure of signal quality indicates that an adaptation of the circuitry 120 is beneficial for the robustness of the system and/or the quality of the obtained signals.

The adaptation decision module 106 may use fixed or adapting thresholds for the at least one measure. The adaptation decision module 106 may also or alternatively select quality indicating measures and/or contextual measures (given by the auxiliary sensors 140) that are to be used depending on the provided data of the measures. Then, the adaptation decision module 106 may compare the one or more selected measures to threshold value(s).

As an alternative, the adaptation decision module 106 may use machine learning and/or multisensory data fusion to identify conditions of the at least one measure of signal quality and input from the auxiliary sensors 140 when an adaptation of the circuitry 120 is beneficial for the robustness of the system and/or the quality of the obtained signals. The machine learning may associate quality indicating measures and contextual measures with potential artifact levels in the acquired signal.

The adaptation decision module 106 may as a further alternative use decision support tools for determining when an adaptation of the circuitry 120 is beneficial for the robustness of the system and/or the quality of the obtained signals based on the received measures.

The circuitry 120 may receive a signal from at least one electrode 122, which obtains a signal representing physiological measurements from a living being. The circuitry 120 may be comprised of at least one filter 124, which may filter out undesired frequencies in the obtained signal, and at least one amplifier 126, which may amplify the filtered signal, for refining the signal. The circuitry 120 may further comprise an analog-to-digital converter 128 for converting the acquired signal to digital domain. Further, the circuitry 120 may comprise an active feedback circuitry 130 for providing an active feedback signal to the living being.

According to an embodiment, the parameter to be controlled may be one or more of a parameter of the filter(s) 124, a parameter of the amplifier(s) 126 and a parameter of the active feedback 130. For instance, the parameter may be a cut-off frequency of the filter(s) 124, a gain of the amplifier(s) 126, or a gain of the active feedback circuitry 130.

The adaptation decision module 106 may transmit information on the signal quality of the received signal to a feature extraction analysis module 108. The feature extraction analysis module may be configured to determine features that are extractable from the received signal depending on the quality of the signal. For instance, if the quality of the signal is too low, some features may not be possible to extract.

The feature extraction analysis module 108 may receive the at least one calculated measure of signal quality, i.e. one or more of the individual and/or combined measures described above. The feature extraction analysis module 108 may also receive one or more contextual measures based on the auxiliary sensors 140. Further, the feature extraction analysis module 108 may receive input on a state of the circuitry 120 for acquisition of the signal, e.g. indicated by controlled parameter values.

The feature extraction analysis module 108 may use machine learning techniques based on the received information to identify and characterize a state of the multiple input values to a potential use of the acquired signal.

A machine learning algorithm may be trained using signals in which potential uses of the acquired signals have already been identified, allowing the machine learning algorithm to characterize different inputs (measures indicating quality, contextual measures, state of the circuitry 120) and correlate the inputs to the identified potential uses.

For example, for a signal indicative of heart activity, such as an electrocardiogram, the feature extraction analysis module 108 may identify the following different qualities of the signal:

the signal is not usable at all;
the signal is usable for peak detections in some specific segments;
the signal is usable for peak detection in most of the signal;
the signal is usable for additional analysis involving shape of the QRST complex;
the signal is of high quality and both morphology and amplitude analyses could be performed.

The control device 100 may be further arranged to output the received signal, possibly together with an indication of which features are extractable, to a further processing device 160 for processing the signal. The further processing device 160 may then process the signal in order to e.g. extract features of the signal, analyze the signal and provide an indication of a condition of the living being based on the analysis. The processing device 160 may for instance be connected to a display for visually presenting the acquired signal in correspondence with the extractable features.

The processing device 160 may be arranged in a common hardware, software or combination of software and hardware as the control device 100. However, it should be realized that the processing device 160 may be provided in separate hardware, software or combination of software and hardware and may be arranged to receive the information from the control device 100 through a wired or wireless connection.

Below, examples of acquisition of capacitively coupled electrocardiogram (ccECG) and acquisition of bioimpedance (BIOZ) are mainly described. However, it should be realized that the control of acquisition of a signal could be equally applied e.g. to obtaining of an EEG; or an EMG signal.

Figure 2:
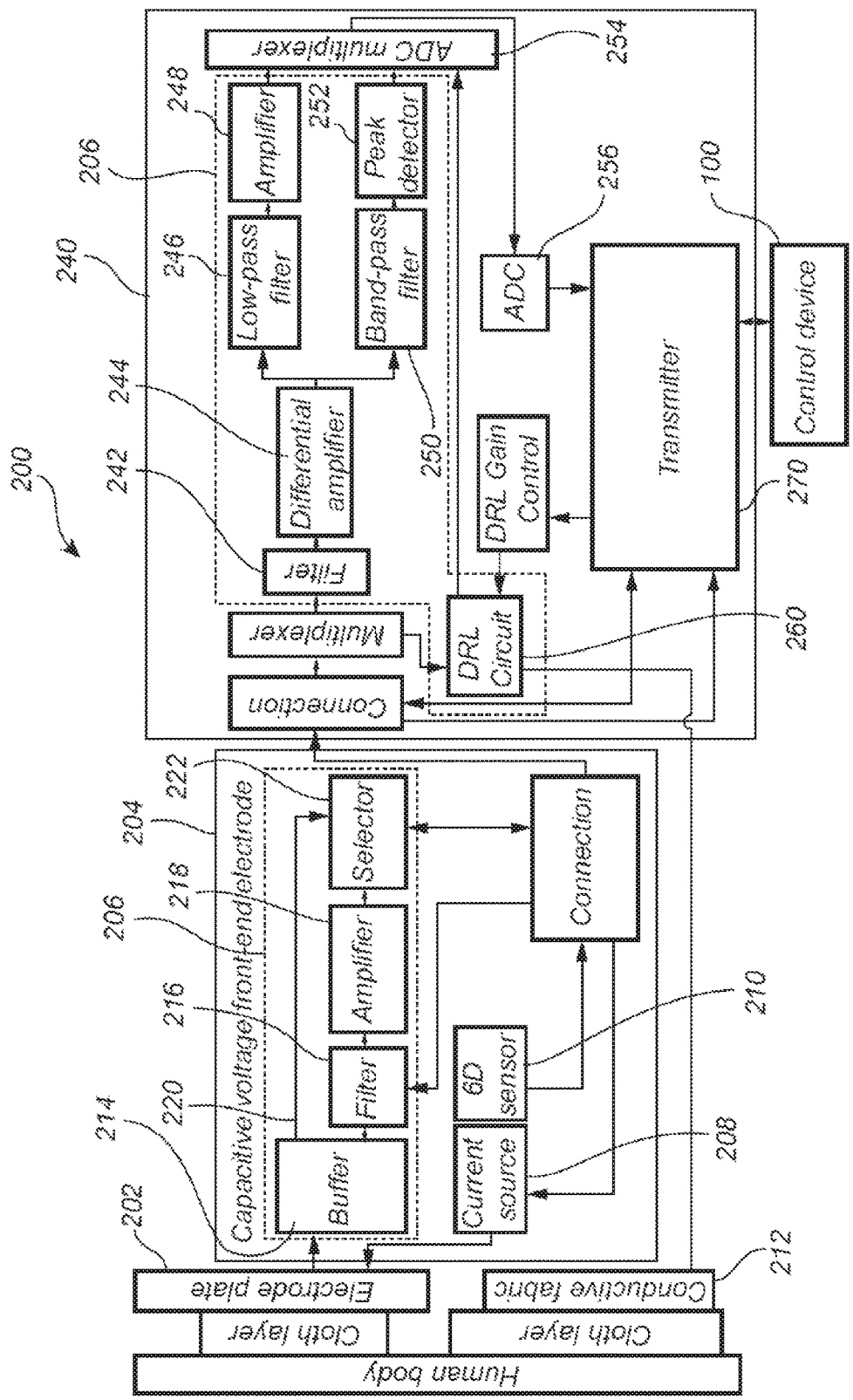
FIG. 2 is a schematic view of a sensor and circuitry for acquisition of a signal according to a first embodiment.

Referring now to FIG. 2, a system 200 comprising a sensor and circuitry for acquisition of a ccECG signal and converting it into digital domain will be described in detail.

The system 200 comprises at least one electrode plate 202, which may be integrated into clothing in order to be arranged in relation to a person and to acquire a ccECG signal. The system further comprises at least one active front-end electrode 204, which may comprise circuitry 206 for refining the signal. The active voltage front-end electrode(s) 204 may further comprise a current source 208 connected to the electrode plate 202 for capacitance measurements and a 6D sensor 210 forming an auxiliary sensor for acquiring additional data.

The system 200 further comprises a conductive fabric 212, which may also be integrated into clothing and may be used for active feedback.

The active voltage front-end electrode(s) 204 together with the conductive fabric 212 may be wired to back-end electronics 240. The back-end electronics 240 may process the acquired signal further, digitalize the signal and may also communicate with a control device 100, e.g. via a wireless connection, such as Bluetooth®. The back-end electronics 240 may also comprise a processing unit (not shown), which may e.g. control sampling and transmission.

The circuitry 206 for refining the signal may comprise a buffer 214 with biasing resistor from input to ground. The biasing resistor together with the (varying) capacitance between the electrode plate 202 and the living being forms an early high-pass filter in the circuitry 206.

In a case of electrode plate to body coupling capacitance of 4 pF, together with a common mode input capacitance of an amplifier of 3 pF, a biasing resistor value of 250 GΩ results in a cut-off frequency of below 0.1 Hz of the early high-pass filter, which does not distort the ECG signal morphology.

An active voltage front-end electrode 204 further comprises a choice of two signal paths from the buffer 214. A first signal path includes a high-pass filter 216 with two or more selectable cut-off frequencies. A first cut-off frequency may provide a cut-off of 0.1 Hz, and the second cut-off frequency may provide a cut-off of 2.8 Hz.

The two or more selectable cut-off frequencies may allow targeting different application environments and imply a trade-off between robustness against motion artifacts and low-frequency signal distortion.

This selectable feature allows the circuitry 206 to be dynamically adapted to improve its robustness when quality of an obtained signal is undesirable (e.g. has low-frequency motion artifacts). This adaptation may prevent saturation of amplifiers that follow and allows acquiring an ECG signal that can at least allow for QRS-detection.

The high-pass filter 216 may be followed by an amplifier 218, which improves the signal. The amplifier 218 may be a variable-gain amplifier, such that the gain of the amplifier 218 may be controlled.

A second signal path 220 bypasses the high-pass filter 216 and amplifier 218, connecting an output of the buffer 214 directly to a signal path selector 222.

The second signal may be used for improving stability of an active feedback loop when needed, in a trade-off with signal robustness.

The signal path selector 222 may receive the signals from both the first and second signal paths 220 and a control parameter may determine which signal that is selected by the signal path selector 222.

The active voltage front-end electrode 204 may also be equipped with a Howland current source 208 for real-time capacitance measurement, which may provide information regarding artifacts caused by a change in distance between electrode and a body of the living being.

An active voltage front-end electrode 204 may further comprise a 6D acceleration and gyroscope sensor 210, which may record local movements of the active front-end electrode 204. The movements recorded by the 6D sensor 210 may be used as additional input for controlling the circuitry 206.

The back-end electronics 240 may support connections for a plurality of active voltage front-end electrodes 204. The signals from the plurality of electrodes 204 may be multiplexed in real time to permit dynamically determining optimal signal locations in an array configuration, or may be recorded in parallel by the back-end electronics 240 to perform computations that require more than one signal. The back-end electronics 240 may thus be arranged to select electrodes 204 to be used from an array of electrodes 204.

Analog output signals from a selected pair of active electrodes 204 may pass a high-pass filter 242 and a differential amplifier 244.

The differentially amplified signal may pass a low-pass filter 246 and may be further amplified in a final amplifier 248 for providing an ECG signal in a first channel.

The differentially amplified signal may also pass a band-pass filter 250, which may further pass a peak detector 252 for providing an impedance signal in a second channel.

The back-end electronics 240 may comprise more than one set of the first and second channels. Hence, the back-end electronics 240 may comprise a plurality of sets of the high-pass filter 242, the differential amplifier 244, the low-pass filter 246, the amplifier 248, the band-pass filter 250, and the peak detector 252 to enable simultaneous recording of more than one signal.

The back-end electronics 240 may further comprise an active feedback circuitry 260. For instance, the active feedback circuitry 260 may comprise a capacitive Driven Right Leg (DRL) circuit, which may be used to eliminate common mode noise by actively canceling an interference. The DRL circuit 260 may receive the analog signals from the selected electrodes 204 and may provide a feedback signal to a conductive fabric, which provides the feedback to the living being for canceling an interference. Dynamic DRL gain adaptation may be included to control instability of a feedback loop.

The first and second channels may be input to an analog-to-digital multiplexer 254 together with the DRL output. Then, the multiplexed signal may be converted to digital form by an analog-to-digital converter 256. The signal in digital form may be further provided to a transmitter 270 for transmitting the signal to the control device 100.

The control device 100 may further be arranged to communicate with the back-end electronics 240 for providing control signals for controlling parameter(s) of the circuitry 206, such as the cut-off frequency of the high-pass filter 216, a gain of the amplifier 218, which signal path to be selected by the signal path selector 222, a gain of the differential amplifier 244, a gain of the differential amplifier 248, and a gain to be used by the DRL circuit 260.

The voltage front-end electrode 204 and the back-end electronics 240 may be arranged on respective printed circuit boards (PCB) and may be connected by a wired connection therebetween. However, it should also be realized that the voltage front-end electrode 204 and the back-end electroncis 240 may be arranged on a common PCB. Further, components of the voltage front-end electrode and the back-end electronics 240 may be divided on to two or more PCBs in other manners.

Figure 3:
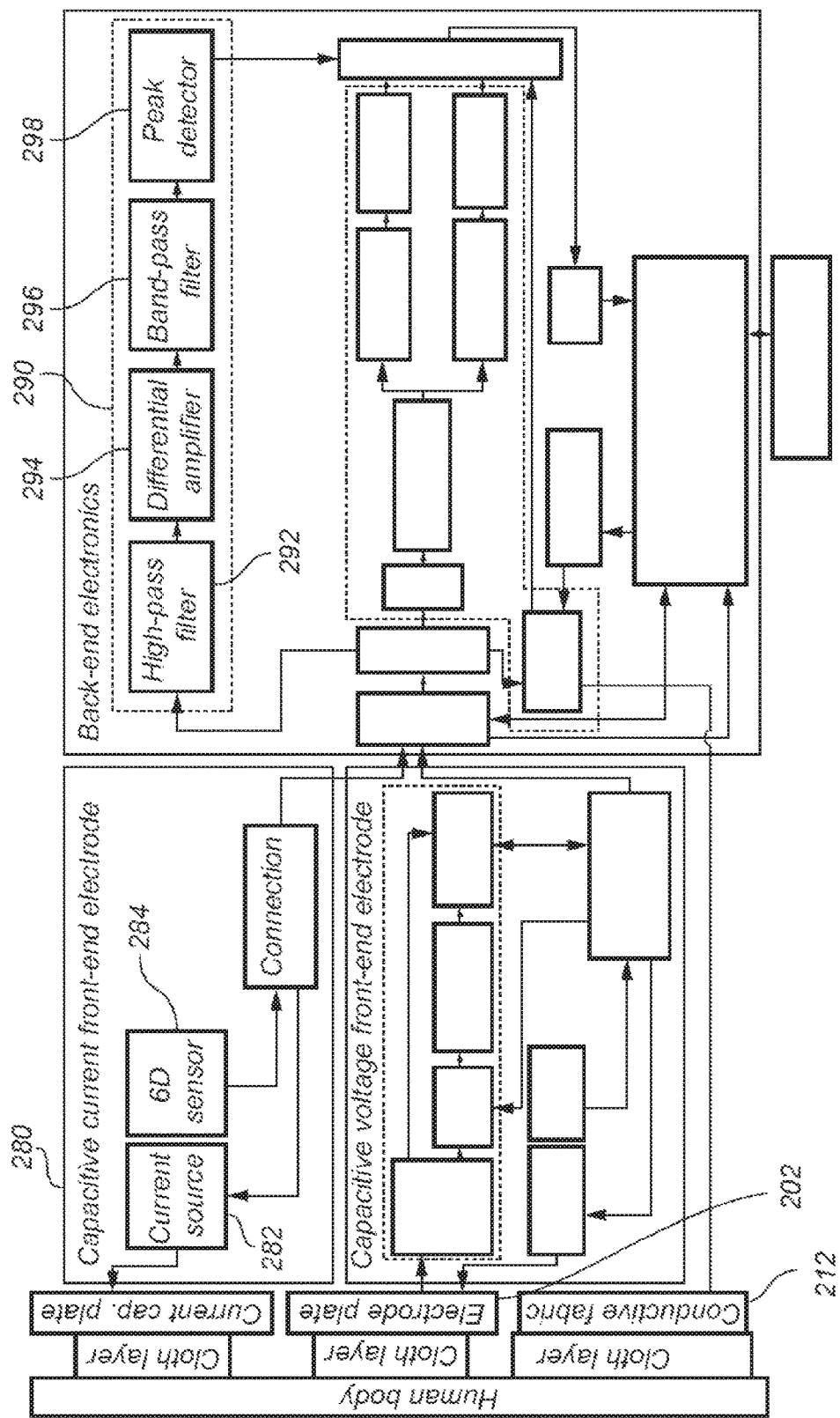
FIG. 3 is a schematic view of a sensor and circuitry for acquisition of a signal according to a second embodiment.

Referring now to FIG. 3, the system 200 is shown to include also a sensor and circuitry for acquisition of a BIOZ signal and converting it to digital domain.

Although the acquisition of the BIOZ signal is shown in combination with acquiring of a ccECG signal, it should be realized that the system could merely acquire the BIOZ signal or that the acquiring of the ccECG signal and/or the BIOZ signal may be combined with acquisition of other signals as well. The BIOZ signal could be used as a measure of respiration of the living being.

The system 200 for acquiring a BIOZ signal comprises at least one capacitive current front-end electrode 280. The at least one capacitive current front-end electrode 280 may comprise an electrode plate and a current source 282.

A pair of capacitive current front-end electrodes 280 may thus be arranged such that a first capacitive current front-end electrode 280 injects and a second capacitive current front-end electrode 280 receives a current through the living being, to which the electrodes are related.

Further, a pair of capacitive voltage front-end electrodes 204 may be arranged to read out a voltage. The voltage front-end electrode 204 may provide signal path selection between two signal paths as described above and a high-pass filter 216 with two selectable cut-off frequencies within the first signal path. In the case of a BIOZ signal, a first cut-off frequency may provide a cut-off of 0.1 Hz, and the second cut-off frequency may provide a cut-off of 0.5 Hz.

The capacitive voltage front-end electrodes 204 may be connected to back-end electronics 240 for further processing. The back-end electronics 240 may thus include at least one BIOZ channel 290, which may process the read out voltage from a pair of electrodes 204.

As described above for the processing of ccECG signal, the back-end electronics 240 may comprise multiple BIOZ channels and BIOZ signals can be read from multiple sets of voltage front-end electrodes 204 working together with multiple sets of capacitive current front-end electrodes 280.

Analog output signals from a selected pair of voltage front-end electrodes 204 may pass a high-pass filter 292 with a cut-off frequency of 1 kHz, and a differential amplifier 294. The differentially amplified signal may pass a band-pass filter 296 at 1 MHz and a peak detector 298, before the signal from the BIOZ channel 290 is passed to the AD multiplexer 254 and the ADC 256 for converting the signal to digital form.

The circuitry for acquisition of the BIOZ signal may be adapted based on assessment of signal quality (as further described below). In this regard, the parameters of the circuitry to be adapted could be the frequency of the injected signal (together with the frequency of the band pass filter 296), the amount of current injected, the gain of the voltage front-end electrode 204, the selectable high-pass filter 216, the signal path selection 222, and the gain of the differential amplifier 294.

Figure 4:
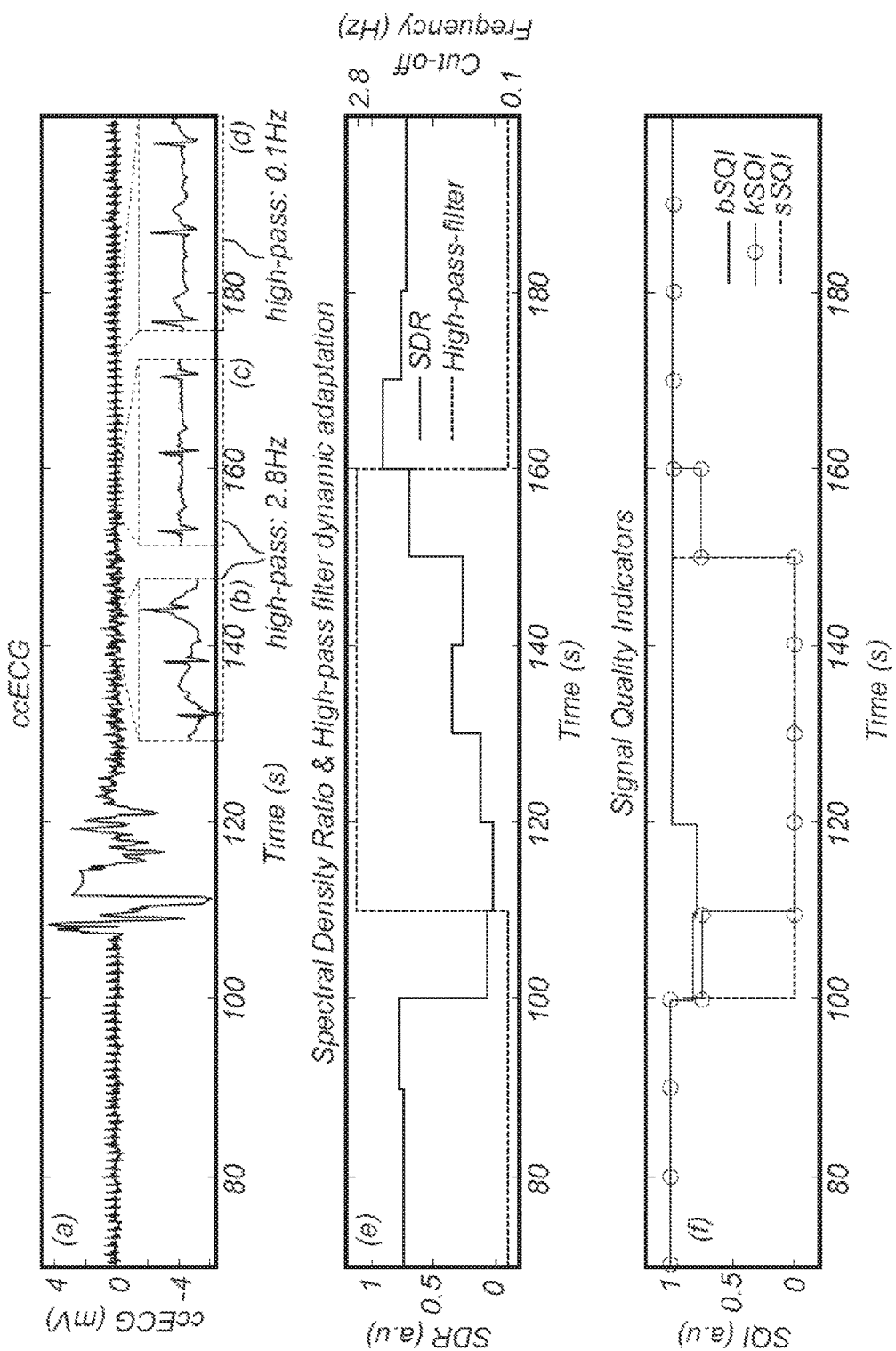
FIG. 4 is an illustration of recorded signals and calculated signal quality indicators for an electrocardiogram measurement.

Referring now to FIG. 4, an example of an ECG signal received by the control device 100 will be discussed and the processing of the signal quality calculation module 104 and the signal adaptation decision module 106 for improving robustness of the acquiring of the signal will be discussed.

The signal quality calculation module 104 may be arranged to calculate three signal quality indicators (SQI) in real-time. The SQIs used may be bSQI, kSQI, and sSQI, as defined in Li, Qiao, et al. "*Robust heart rate estimation from multiple asynchronous noisy sources using signal quality indices and a Kalman filter*", Physiol. Meas. 2008 January; 29(1): 15-32.

Also, a spectral density ratio (SDR), as defined in the article, calculated for the sSQI may be used to validate performance of dynamic adaptation of the circuitry to environmental conditions.

The signal adaptation decision module 106 may be arranged to determine whether the circuitry 206 is to be controlled to change the cut-off frequency of the filter 216 between 0.1 Hz and 2.8 Hz.

FIG. 4 shows at (a) a ccECG signal acquired under changing environmental conditions. Further, FIG. 4 shows at (b) a close-up on signal quality in time intervals with an induced motion, at (c) without motion when the high-pass filter was increased to 2.8 Hz and at (d) without motion when the high-pass filter was restored to 0.1 Hz for full ECG waveform recording.

FIG. 4 further shows at (e) SDR and high-pass filter adaptation in response to it, and at (f) the three SQIs.

The signal quality calculation module 104 may calculate the SQIs at regular intervals and may provide averaged SQIs, which may use a plurality of calculated respective SQIs over a time period, to the signal adaptation decision module 106.

In the example shown in FIG. 4, SDR and sSQI parameters were calculated every 10 s, while bSQI and kSQI were calculated every 2.5 s and averaged every 10 s.

As illustrated in FIG. 4, dynamic adaptation may prevent saturation of amplifiers and allows to obtain a lower-quality, still distinguishable signal when a motion artifact is occurring, instead of completely losing the ccECG signal.

Thus, the signal may comply with ambulatory standards when possible, while avoiding signal loss otherwise. Further, as can be seen from (c) and (d) in FIG. 4, the higher frequency high-pass filter 216 may present a distortion mainly on a T-wave of the signal, but quality is restored once the filter 216 is configured back to 0.1 Hz in response to a good quality indicated by the SDR.

Using these SQIs, validation of the adaptation of the circuitry was performed by measuring 4 subjects while doing normal office work on a computer for 40 minutes with the system 200 integrated into an office chair. Dynamic adaptation was performed half of the time and the remaining time the high-pass filter 216 was fixed to 0.1 Hz.

Results are shown in Table 1 below in terms of percentage of time the signal was suitable for beat detection (bSQI>0.6), for higher quality monitoring (SDR>0.5), with a kSQI>0.5, and saturated (visually identified). Also, the table indicates mean values of bSQI, SDR and kSQI.

TABLE 1

Adaptive robustness validation results.

| Condition | Adapting feature ON | Adapting feature OFF |
|---|---|---|
| bSQI >0.6 | 68.0% (mean = 0.67) | 69.6% (mean = 0.69) |
| SDR >0.5 | 19.8% (mean = 0.30) | 2.5% (mean = 0.12) |
| kSQI >0.5 | 35.2% (mean = 0.49) | 13.3% (mean = 0.25) |
| Saturated signal | 10.4% | 36.8% |

Table 1 shows a significant improvement in terms of SDR, kSQI and saturated signal when using the adaptation of the circuitry. The bSQI values are found equivalent, possibly because bSQI has the disadvantage that it can output good values in presence of noise/saturation as long as both beat detectors coincide on "false beats".

In this use-case, the proposed adaptive system and algorithm would enable the recording of full ECG morphology under certain conditions, which implies the possibility for long term recordings. As indicated in Zimetbaum, Peter J., et al., "*Diagnostic yield and optimum duration of continuous-loop event monitoring for the diagnosis of palpitations: a cost-effectiveness analysis*", Annals of Internal Medicine, 128.11 (1998): 890-895, this could increase the diagnostic yield of 15%-39% that the limited 24-hours Holter monitoring brings in the identification of heart rhythm disorders. Also; long term recordings can provide first indications of different cardiac pathologies that require more information than heart rate and heart rate variability.

The electrode 204 may be integrated into clothes worn by a person, in a chair in which the user sits or in a bed linen for monitoring a person when sleeping or lying in bed. Such electrodes may be especially suited for ambulatory use in long term recording and monitoring of a condition of a person.

The electrode 204 may also be of interest in a clinical environment wherein use of standard wet electrodes cannot be used or implies high inconvenience to the patient, e.g. neonates, burn patients, etc.

Figure 5:
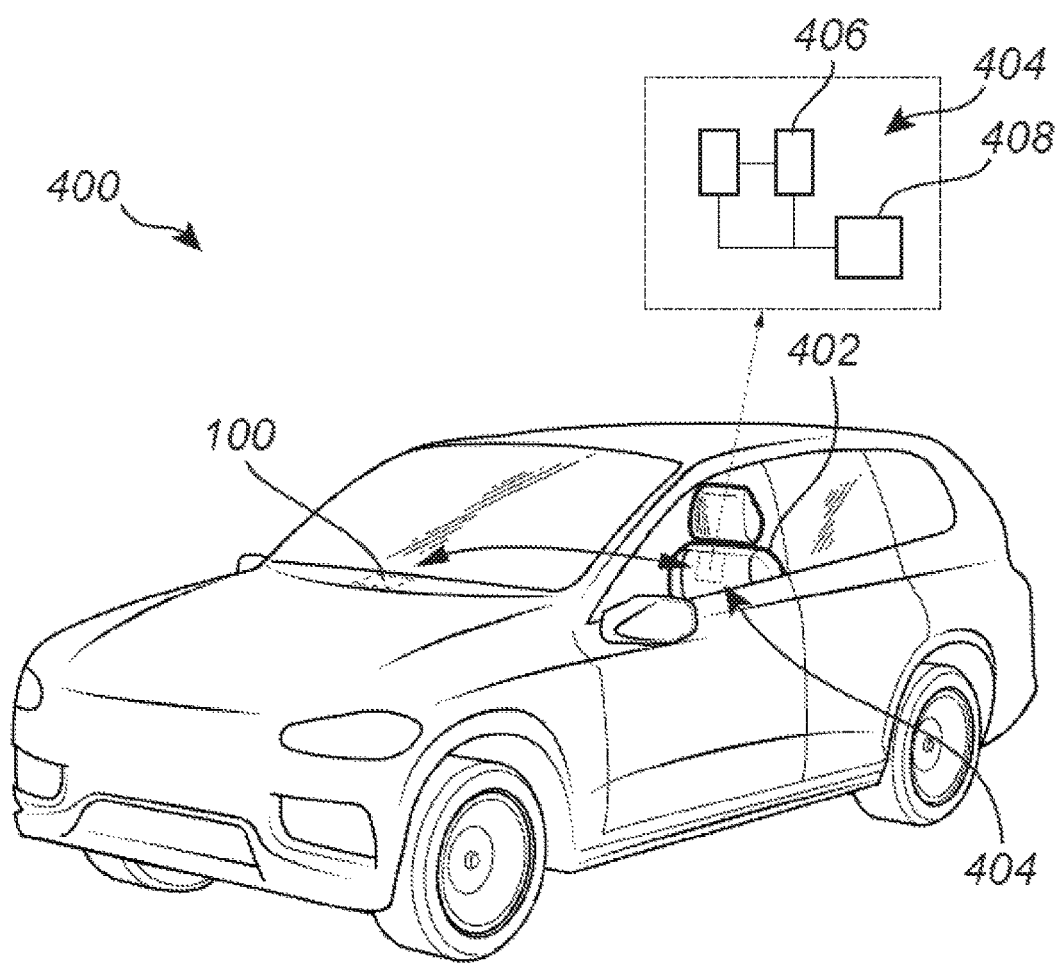
FIG. 5 is a schematic view of a car-installed condition monitoring system for monitoring a person according to an embodiment.

Referring now to FIG. 5, a car-installed condition monitoring system 400 for monitoring a person is shown. The system 400 may monitor a person while seated in a seating 402 of the car.

The system 400 may comprise a sensor unit 404, which may be mounted in the seating 402. The sensor unit 404 may comprise at least one electrode pair 406 arranged to acquire a signal representing a physiological measurement. The sensor unit 404 may further comprise processing circuitry 408 for processing the signal representing the obtained physiological measurement and for controlling acquisition of the signal. The processing circuitry 408 need not necessarily be arranged in a common housing with the electrode pair 406, but may alternatively be mounted e.g. inside the seating 402 or below the seating 402.

The sensor unit 404 may further be connected via a wired or a wireless connection to a control device 100, as described above, that may control acquisition of the signal. The control device 100 may be arranged in a common housing of the sensor unit 404. However, the control device 100 may alternatively be implemented in a separate unit, e.g. within a central processing unit of the car.

The control device 100 may ensure that the signal quality is dynamically adapted such that a useful signal may be provided during a large percentage of time, during driving of the car. The system 400 thus enables acquiring of a useful signal even when driving the car in harsh driving conditions, which may cause vibrations to the seating 402 from the road.

The auxiliary sensors for the car-installed condition monitoring system 400 may include a vibration sensor, which may also be mounted in the seating 402, or alternatively in the sensor unit 404, for sensing vibrations of the seating 402 during driving of the car. For instance, the vibration sensor may be a 3-axis gyroscope sensor.

The physiological measurement acquired by the sensor unit 404 may be used in a car control system in various manners, based on the physiological measurement alone or in combination with input from other sensors.

A health condition of the person seated in the car may be monitored, e.g. by performing periodic, such as daily or weekly, checks of a driver. Thus, a health condition may be monitored when the driver is anyway seated in the car, e.g. to enable identification of abnormal conditions. Changes in heart and respiratory activity may be identified and may be used for alerting the driver to do a more thorough check. Also, sudden changes in the health condition, e.g. due to heart failure, may be identified. Such detections may be used by the car control system to safely bring the car to a halt.

Further, the physiological measurement acquired by the sensor unit 404 may be used in the car control system, possibly in combination with input from other sensors, for monitoring whether a capacity of the driver to safely drive the car. The car control system may thus monitor for drowsiness or attention level of the driver and/or detect a stress level of the driver. The car control system may also provide feedback based on an undesired condition of the driver, e.g. to alert the driver to take a break.

Figure 6:
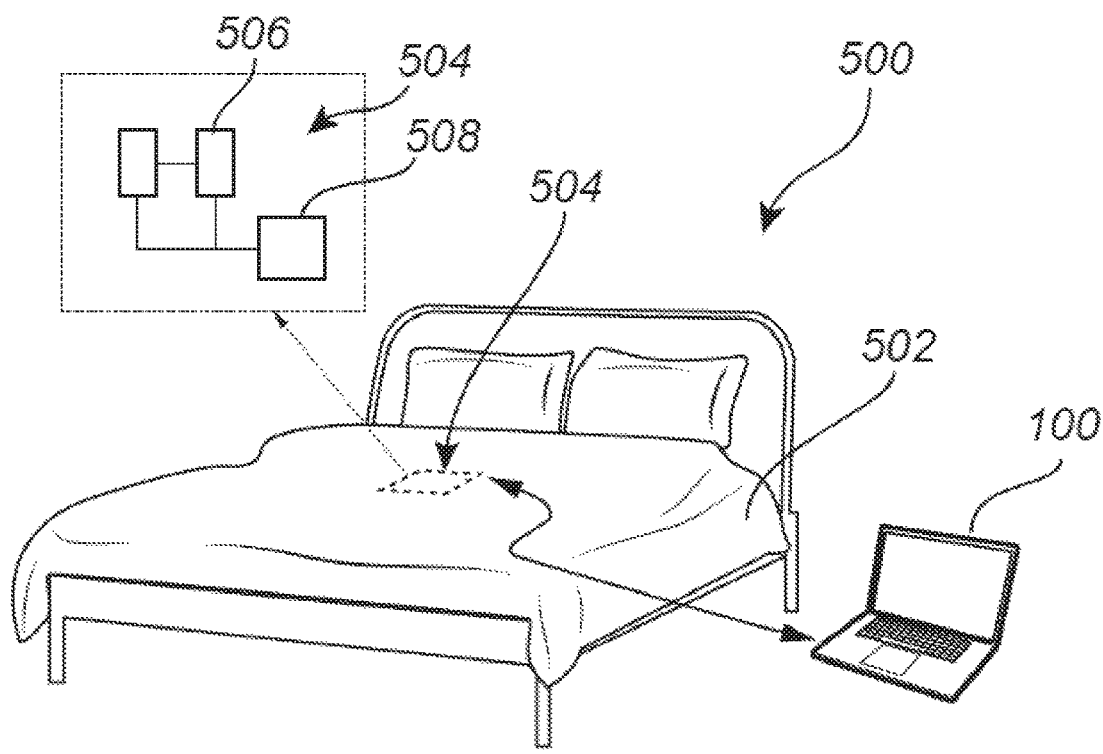
FIG. 6 is a schematic view of a sleep monitoring system according to an embodiment.

Referring now to FIG. 6, a sleep monitoring system 500 is described. The sleep monitoring system 500 may monitor a person while lying in bed sleeping.

The system 500 may comprise a sensor unit 504, which may be mounted in a mattress 502 or in bed linen. The sensor unit 504 may comprise at least one electrode pair 506 arranged to acquire a signal representing a physiological measurement. The sensor unit 504 may further comprise processing circuitry 508 for processing the signal representing the obtained physiological measurement and for controlling acquisition of the signal. The processing circuitry 508 need not necessarily be arranged in a common housing with the electrode pair 506, but may alternatively be mounted e.g. inside the mattress 502 or below the bed.

The sensor unit 504 may further be connected via a wired or a wireless connection to a control device 100, as described above, that may control acquisition of the signal. The control device 100 may be arranged in a common housing of the sensor unit 504. However, the control device 100 may alternatively be implemented in a separate unit, e.g. within a central processing unit of a computer or another external device that may communicate with the sensor unit 504.

The control device 100 may ensure that the signal quality is dynamically adapted such that a useful signal may be provided during a large percentage of time, while a person is lying in bed. The system 500 thus enables acquiring of a useful signal even when the person changes position or takes deep breaths during sleep.

The physiological measurements acquired may be used for analysis of sleep and may be used by a person for improving sleeping habits. The sleep monitoring system 500 may be used for potentially identifying sleep-related diseases such as sleep apnea. Monitoring of the health condition can be performed during a long screening time at the person's home under comfortable conditions, and could be an additional tool to polysomnography (PSG) tests, which need to be performed at a hospital and therefore are limited in time and with reduced comfort.

The physiological measurements acquired may also or alternatively be used for monitoring a health condition of the person while lying in bed. Thus, the system 500 may also be used in a hospital, such that patients may be monitored and alerts may be sent to caregivers if an abnormal condition of a patient is registered.

For the BIOZ signal, the signal quality calculation module 104 could be arranged to calculate a signal quality by means of the SDR with frequency limits defined at different values than the ones used for the SDR in ECG (i.e focusing on physiological respiration rate frequencies). In the same sense the sSQI can be calculated based on this modified SDR. Kurtosis can also be calculated and kSQI with limits to be defined experimentally is another feasible SQI for BIOZ. bSQI could not be used for BIOZ since it is based on QRS peak detection.

In addition, changes in the frequency, amplitude and current of the injected signal used for BIOZ, which is injected by the electrode 280 to the body, can be made in order to test the response of the acquired signal in the BIOZ channel 290, and distinguish between what is noise and what is signal, providing information of the need to perform adaptation to the acquisition circuitry.

Figure 7:
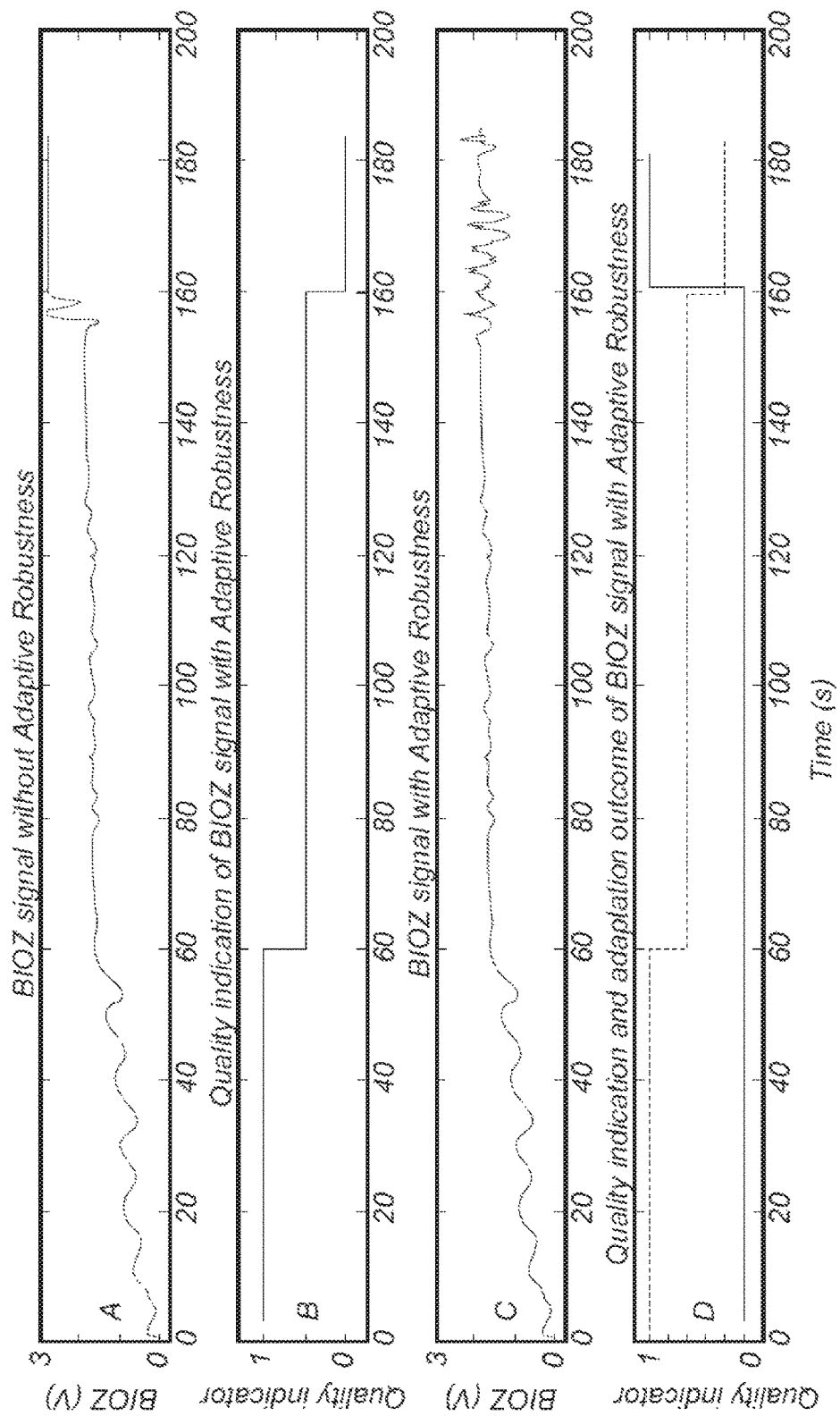
FIG. 7 is an illustration of recorded signals and calculated signal quality indicators for a bioimpedance measurement.

Referring now to FIG. 7, an example of a BIOZ signal received by the control device 100 will be discussed and the processing of the signal quality calculation module 104 and the signal adaptation decision module 106 for improving robustness of the acquiring of the signal will be discussed.

FIG. 7 shows in trace A that motion artifacts in a time region from 155 s to 180 s generate a saturation of the signal. Further, FIG. 7 shows in trace B that a measure indicating quality is showing a mid-quality and low-quality of the signal in different regions.

FIG. 7 illustrates in trace C, a signal using dynamic adaptation of the processing circuitry 206. As indicated in trace D, the signal quality indicator may be used to identify that adaptation is to be applied when motion artifacts occur. The adaptation may then apply a more robust high-pass filtering and, hence, prevent signal saturation. The acquired signal may be distorted due to the filtering and the motion artifacts, but probabilities of acquiring a usable signal is improved. Thus, as shown in trace C, a respiration rate may still be determined while a motion artifact occurs.

Figure 8:
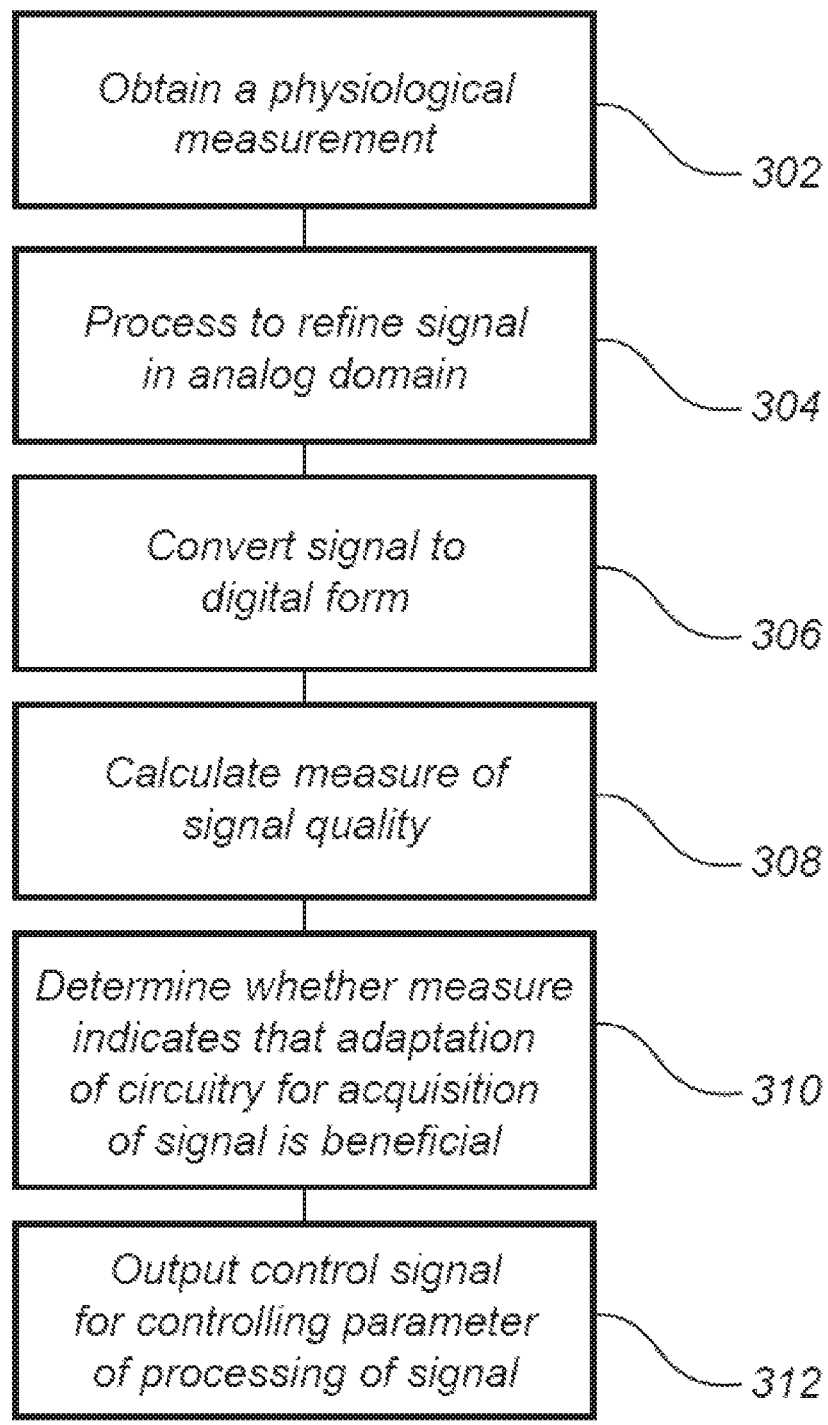
FIG. 8 is a flow chart illustrating a method according to an embodiment.

Referring now to FIG. 8, a method 300 for acquisition of a signal representing a physiological measurement will be generally described.

The method comprises obtaining, step 302, a physiological measurement on a living being. The physiological measurement may be performed using a sensor comprising at least one electrode for acquiring a signal representing the physiological measurement. The physiological measurement may for instance be an ECG; an EEG; an EMC or a bioimpedance.

The signal is then processed, step 304, to refine the signal in analog domain. This may imply that the signal is filtered and amplified.

The refined signal is converted, step 306, to digital form. The converted signal may be transferred to a control device 100 which may further analyze the signal in digital domain.

Thus, at least one measure of signal quality may be calculated, step 308. The measure of signal quality may then be analyzed to determine, step 310, whether the at least one measure of signal quality indicates that an adaptation of circuitry for acquisition of the signal in analog domain is beneficial for the robustness of the system and/or the quality of the obtained signals.

If an adaptation of circuitry is beneficial for the robustness of the system and/or the quality of the obtained signals, a control signal may be output, step 312, for controlling a parameter of processing of the signal in analog domain.

The present disclosure has mainly been described with reference to a limited number of embodiments. However, as is readily appreciated by a person skilled in the art, other embodiments than the ones disclosed above are equally possible within the scope of the present disclosure, as defined by the appended claims.

For example, it should be realized that, in addition to at least one electrode without galvanic contact with the living being, a system may further comprise other sensors and/or electrodes, which may or may not be in galvanic contact with the living being, for acquiring further measurements which may be used in combination with the physiological measurements acquired by the at least one electrode without galvanic contact.

While some embodiments have been illustrated and described in detail in the appended drawings and the foregoing description, such illustration and description are to be considered illustrative and not restrictive. Other variations to the disclosed embodiments can be understood and effected in practicing the claims, from a study of the drawings, the disclosure, and the appended claims. The mere fact that certain measures or features are recited in mutually different dependent claims does not indicate that a combination of these measures or features cannot be used. Any reference signs in the claims should not be construed as limiting the scope.

What is claimed is:

1. A device for controlling acquisition of a signal representing a physiological measurement on a living being, the device comprising:
    an input for receiving the signal in digital form, wherein the signal (i) has been acquired by means of an electrode without galvanic contact between the electrode and the living being, and (ii) has been processed by circuitry for acquisition of the signal in analog domain, the processing of the signal by the circuitry occurring before the signal is converted from analog to digital domain;
    a signal quality calculation module configured to determine a measure of signal quality based on the received signal; and
    an adaptation decision module configured to:
        based on the determined measure of signal quality, detect a trigger to affect amplifier saturation in the processing of the signal by the circuitry, and
        in response to detecting the trigger, control a parameter of the circuitry that affects the amplifier saturation in the processing of the signal by the circuitry.

2. The device according to claim 1, wherein controlling a parameter of the circuitry comprises outputting a control signal that controls a gain of an amplifier.

3. The device according to claim 1, further comprising a feature extraction analysis module being configured to receive input from the adaptation decision module on the signal quality of the received signal and to determine features that are extractable from the received signal.

4. The device according to claim 1, wherein the adaptation decision module is configured to receive input from auxiliary sensors and is further configured to consider the received input from auxiliary sensors in determining whether an adaptation of the circuitry for acquisition of the signal in analog domain is beneficial.

5. The device according to claim 1, wherein the adaptation decision module is configured to compare the at least one measure of signal quality to a threshold value and determine whether the at least one measure of signal quality indicates that an adaptation of the circuitry for acquisition of the signal is beneficial based on a relation between the at least one measure and the threshold value.

6. The device according to claim 1, wherein the acquired signal is a measurement of capacitively coupled electrocardiogram, ccECG.

7. A system for acquisition of a signal representing a physiological measurement on a living being, the system comprising:
    a device according to claim 1;
    a sensor for obtaining a physiological measurement on a living being, the sensor comprising at least one electrode arranged to acquire a signal representing physiological measurement without the at least one electrode being in galvanic contact between the electrode and the living being; and processing circuitry for processing the signal representing the obtained physiological measurement.

8. The system according to claim 7, wherein the processing circuitry comprises an amplifier for amplifying the signal.

9. The system according to claim 7, wherein the processing circuitry comprises a filter for filtering out undesired frequencies of the signal.

10. The system according to claim 7, further comprising a feature extraction module configured to receive the signal in digital form and receive input from an feature extraction analysis module regarding features that are extractable from the received signal, the feature extraction module being configured to process the received signal based on the input from the feature extraction analysis module.

11. A car-installed condition monitoring system for monitoring a person, the condition monitoring system comprising:
a device according to claim 1;
a sensor for obtaining a physiological measurement on the person, the sensor comprising at least one electrode arranged to acquire a signal representing physiological measurement without the at least one electrode being in galvanic contact between the electrode and the person, the sensor being mounted in a seating of the car for monitoring the person while seated in the seating; and
processing circuitry for processing the signal representing the obtained physiological measurement.

12. A sleep monitoring system, comprising:
a device according to claim 1;
a sensor for obtaining a physiological measurement on a person, the sensor comprising at least one electrode arranged to acquire a signal representing physiological measurement without the at least one electrode being in galvanic contact between the electrode and the person, the sensor being mounted in a mattress or bed linen for monitoring the person while lying on the mattress; and
processing circuitry for processing the signal representing the obtained physiological measurement.

13. The device according to claim 1, wherein controlling a parameter of the circuitry comprises outputting a control signal that controls a cut-off frequency of a filter.

14. The device according to claim 1, wherein controlling a parameter of the circuitry comprises outputting a control signal that controls a gain of an active feedback circuitry.

15. The device according to claim 1, wherein the determined measure of signal quality is indicative of degradation of the signal during acquisition without galvanic contact or the existence of irrelevant noise, including motion artifacts.

16. A portable, clothing-oriented condition monitoring system for monitoring a person, the condition monitoring system comprising:
a device according to claim 1;
a sensor for obtaining a physiological measurement on the person, the sensor comprising at least one electrode arranged to acquire a signal representing physiological measurement without the at least one electrode being in galvanic contact between the electrode and the person, the sensor being mounted on one area of the body or clothes thereon, or distribute the analysis across smaller, less intrusive sensors; and
processing circuitry for processing the signal representing the obtained physiological measurement.

17. A method for acquisition of a signal representing a physiological measurement on a living being, the method comprising:
obtaining a physiological measurement on a living being using a sensor comprising at least one electrode arranged to acquire a signal representing physiological measurement without the at least one electrode being in galvanic contact between the electrode and the living being;
processing the signal to refine the signal in analog domain;
converting the refined signal to digital form;
calculating at least one measure of signal quality based on the signal in digital form;
determining whether the at least one measure of signal quality indicates that an adaptation of circuitry for acquisition of the signal in analog domain is beneficial; and
outputting a control signal for controlling a parameter for processing of the signal to refine the signal in analog domain.

18. The method according to claim 17, wherein the controlled parameter is a parameter affecting amplifier saturation in processing of the signal.

19. A computer program product comprising a computer-readable medium with computer-readable instructions such that when executed on a processing unit the computer program product will cause the processing unit to perform a method for controlling acquisition of a signal representing a physiological measurement on a living being, the method comprising:
receiving the signal in digital form, wherein the signal has been acquired by means of at least one electrode without galvanic contact between the electrode and the living being and has been processed by circuitry for acquisition of the signal in analog domain to refine the signal before the signal is converted from analog to digital domain;
calculate at least one measure of signal quality based on the received signal;
determine whether the at least one measure of signal quality indicates that an adaptation of the circuitry for acquisition of the signal in analog domain is beneficial; and
in response to the determination that an adaptation of the circuitry for acquisition of the signal is beneficial, output a control signal for controlling a parameter of the circuitry for acquisition of the signal in analog domain, wherein the controlled parameter is a parameter affecting amplifier saturation in processing of the signal by the circuitry.

* * * * *